United States Patent [19]

Siposs

[11] Patent Number: 4,806,135
[45] Date of Patent: Feb. 21, 1989

[54] BUBBLE TRAP FOR PHASE-SEPARATING GAS BUBBLES FROM FLOWING LIQUIDS

[76] Inventor: George G. Siposs, 2930G Grace La., Costa Mesa, Calif. 92626

[21] Appl. No.: 162,608

[22] Filed: Mar. 1, 1988

[51] Int. Cl.⁴ ............................................. B01D 19/00
[52] U.S. Cl. ...................................... 55/204; 55/178; 55/459.1; 210/304; 210/456; 210/512.1
[58] Field of Search ............... 55/178, 201, 204, 459.1; 210/136, 188, 304, 436, 456, 512.1

[56] References Cited

U.S. PATENT DOCUMENTS

| | | | |
|---|---|---|---|
| 3,715,863 | 2/1973 | Zanoni | 55/204 |
| 3,827,562 | 8/1974 | Esmond | 210/304 |
| 3,891,416 | 6/1975 | Leonard et al. | 55/178 |
| 3,939,078 | 2/1976 | Servas et al. | 210/436 |
| 3,993,461 | 11/1976 | Leonard et al. | 55/178 |
| 4,038,194 | 7/1977 | Luceyk et al. | 210/436 |
| 4,157,965 | 6/1979 | Raible | 55/178 X |
| 4,208,193 | 6/1980 | Munsch et al. | 55/178 X |
| 4,243,531 | 1/1981 | Crockett et al. | 55/178 X |
| 4,344,777 | 8/1982 | Siposs | 55/201 X |
| 4,345,919 | 8/1982 | Wilkinson et al. | 55/204 X |
| 4,368,118 | 1/1983 | Siposs | 55/178 X |
| 4,394,138 | 7/1983 | Schilling | 55/459.1 X |
| 4,411,783 | 10/1983 | Dickens et al. | 55/204 X |
| 4,490,254 | 12/1984 | Gordon et al. | 210/436 X |
| 4,572,724 | 2/1986 | Rosenberg et al. | 55/178 X |
| 4,642,089 | 2/1987 | Zupkas et al. | 55/178 X |
| 4,664,682 | 5/1987 | Monzen | 55/178 |
| 4,690,762 | 9/1987 | Katsura | 55/178 |
| 4,737,139 | 4/1988 | Zupkas et al. | 55/178 X |

Primary Examiner—Robert Spitzer
Attorney, Agent, or Firm—Allen A. Dicke, Jr.

[57] ABSTRACT

Bubble trap has a hollow body with an upwardly directed mixed fluid inlet on its side directed to introduce mixed fluid in a tangential direction so as to rotate the liquid within the body. This rotation permits separation of the gas bubbles from the liquid and permits withdrawal of the debubbled liquid from the bottom of the body. The inlet and outlet from the body are respectively upwardly and downwardly directed to permit draping of inlet and outlet hoses. In one embodiment, a filter is installed to facilitate gas bubble separation.

10 Claims, 2 Drawing Sheets

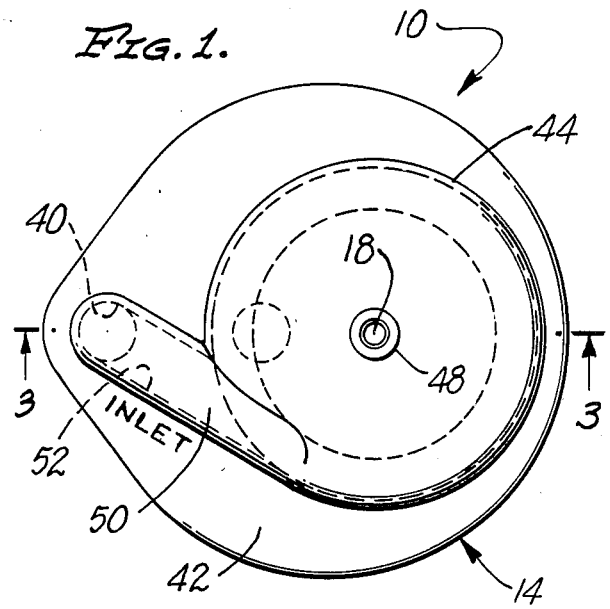
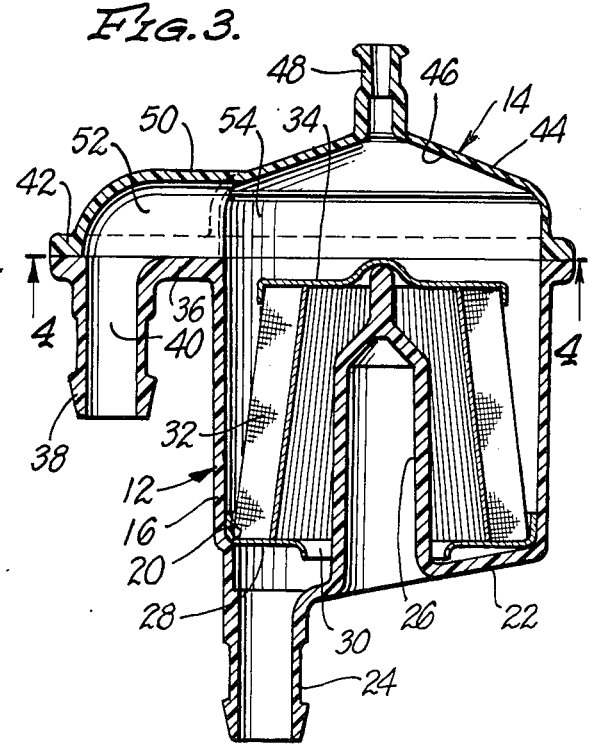
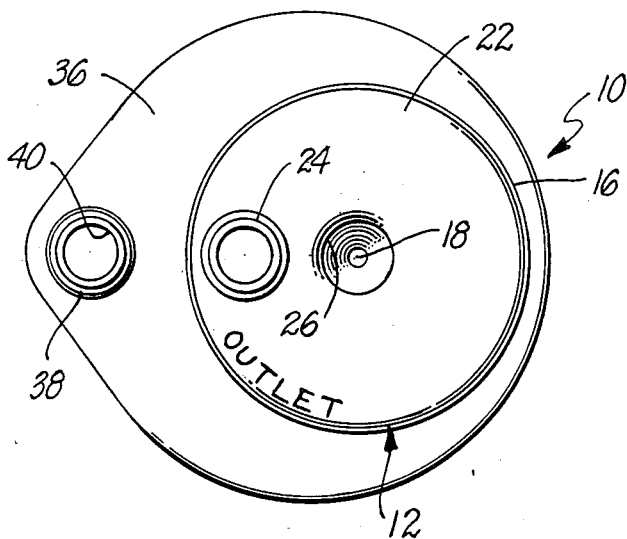
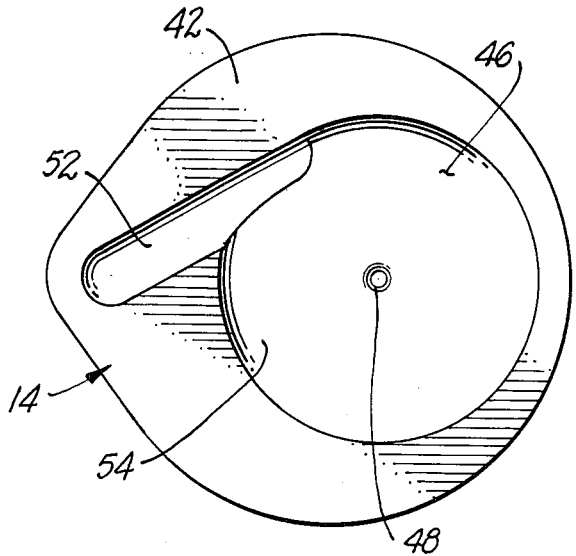

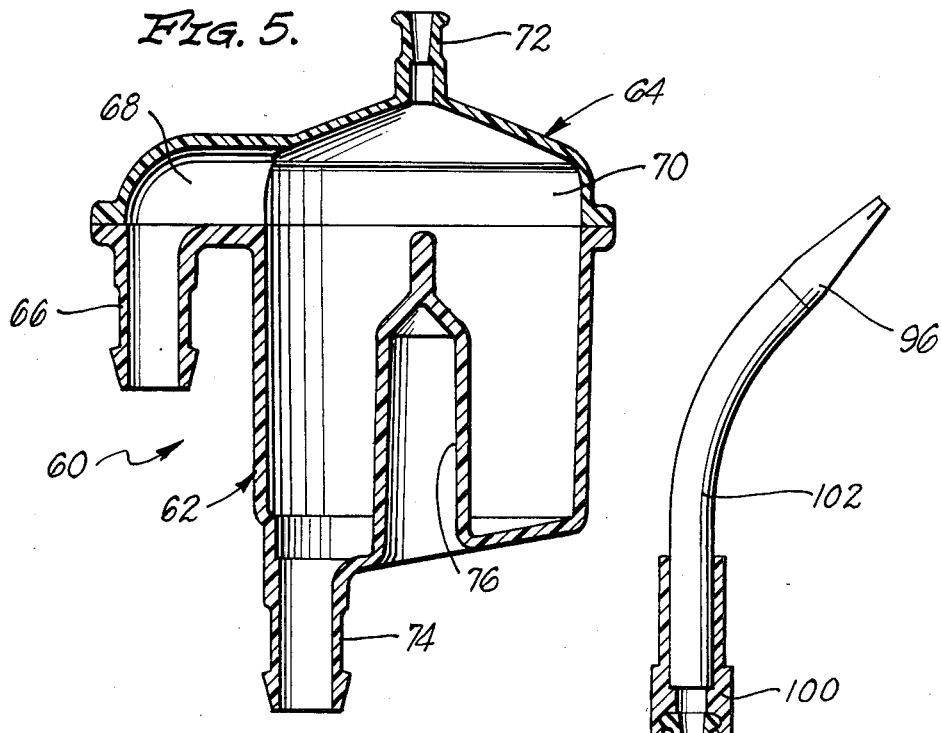
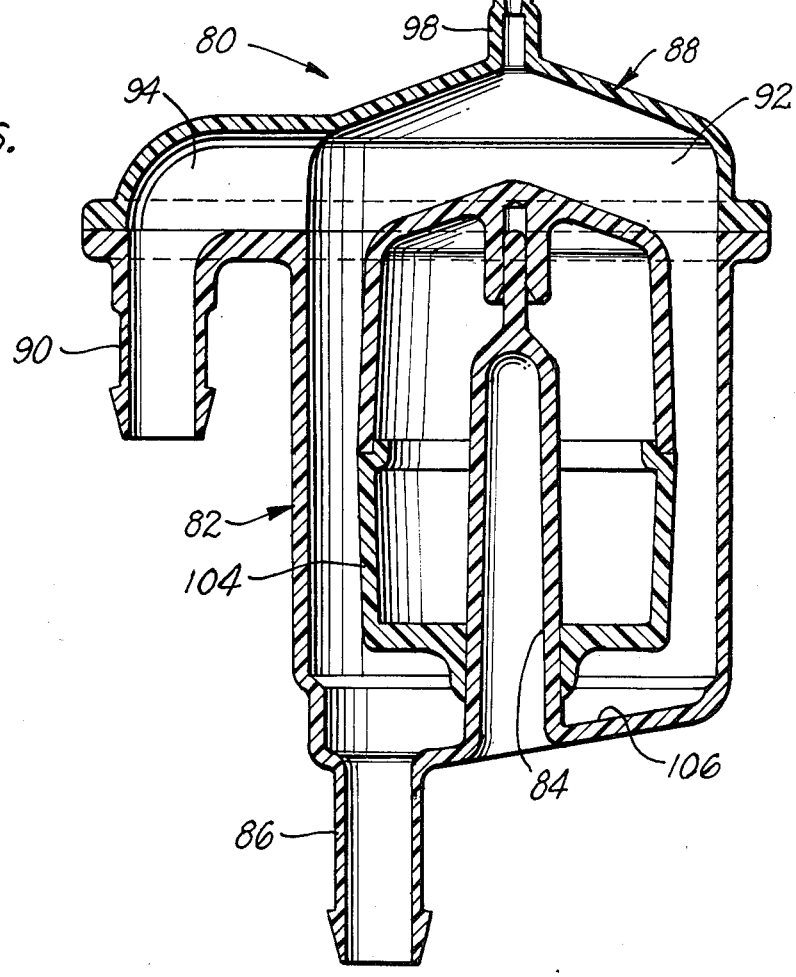

4,806,135

BUBBLE TRAP FOR PHASE-SEPARATING GAS BUBBLES FROM FLOWING LIQUIDS

FIELD OF THE INVENTION

This invention is directed to the separation of gas bubbles from flowing liquid systems, particularly cardio-pulmonary bypass circuits employed during open-heart operations to separate air emboli from the flowing blood.

BACKGROUND OF THE INVENTION

In hydraulic circuits which contain moving fluids, it is frequently necessary to eliminate gas bubbles before they reach functional parts. A specialized example of such a circuit is a cardio-pulmonary bypass circuit employed during open-heart procedures. If blood in such a circuit contains air or gas emboli, it is imperative to remove such emboli (i.e. bubbles) before they reach the patient. Otherwise, the emboli may cause serious neurological damage or death. Blood-separating devices in cardio-pulmonary circuits are usually placed between the arterial pump and the patient so that air emboli are removed before the blood reaches the patient. Many surgical teams use arterial filters to serve as a bubble trap. The filter does not allow bubbles to pass through the tiny filter openings. The problem is that the openings must be very small to be effective bubble stops, and such small openings may cause harm to the delicate red blood cells. There is, thus, a need for a phase-separating device which passes blood atraumatically and separates air. The air may be separated and returned to the oxygenator to recover any physiological liquids delivered therewith. Similar problems exist with other physiological fluids which may be found in the operating field.

There are several bubble traps presently available. One has a large internal volume, and thus wastes a great deal of blood, and it has to be disassembled and cleaned after every operation because it is not a disposable device. Another device is made from polymer composition material and is pre-sterilized and disposable. This device separates bubbles from the blood by relying on circular flow, but the problem is that there are internal flow-directing vanes which present a large surface area. The edges of the vanes may cause trauma to red blood cells as they impinge upon the vanes during flow. Furthermore, the large surface area may be harmful because it is known that any surface contact with blood may cause platelet damage. Thus, it is desirable to minimize the surface area in contact with the flowing blood.

Another commercially available separator is made of polymer material and is disposable. It relies on circular flow, and to achieve this flow, the blood inlet fitting is tangentially directed. The inlet is a side fitting positioned in the horizontal plane, and the attachment of tubing thereto becomes difficult because in normal circumstances, the tubing will hang and may pinch. The tubing does not drape naturally from such a side fitting.

Examples of two prior bubble trap structures are found in George G. Siposs U.S. Pat. Nos. 4,344,777 and 4,368,118.

There is need for a simple, disposable device which can be inexpensively produced and pre-sterilized. Such a device needs to separate gas bubbles from a moving stream of physiological liquid, such as blood, without being unnecessarily complex. Furthermore, the device must have a minimum blood contact surface and must have no structure inside the device with which the flowing liquid would be in contact which could cause trauma to the delicate blood cells. In addition, the device must have a minimum interior volume to minimize blood loss. Also, the device must have a minimum number of easy-to-produce parts to be trouble-free and inexpensive.

SUMMARY OF THE INVENTION

In order to aid in the understanding of this invention, it can be stated in essentially summary form that it is directed to a bubble trap for phase-separating gas bubbles from flowing liquids, particularly physiological liquids, and comprises a body with a circular section. The side of the circular body has a side arm thereon with an upwardly directed inlet. The side arm is tangentially connected to the body so that upwardly moving mixed liquid turns and causes horizontal rotation of the mixed liquid within the body. This rotation encourages separation of gas and air bubbles from the liquid. The body has a downwardly directed bottom outlet for the liquid. In another embodiment, the body contains therein a filter which filters large solids from the blood. In such a case, the outlet is at the bottom of the body and receives flow from the interior of the filter.

It is thus an object and advantage of this invention to provide a bubble trap for phase-separating gas bubbles from flowing liquids, and particularly physiological liquids wherein the bubble trap has a hollow body of minimum size, minimum contact area, and is tangentially supplied with in-flowing liquid so that rotation of the liquid within the body causes bubble separation.

It is another object and advantage of this invention to provide a bubble trap which has vertical inlet and outlet fittings so as to allow the connected fluid filled lines to drape naturally and provide a body which has a circular shape and a tangential flow near the top, to cause rotation within the body without the need for flow-directing vanes.

It is a further object and advantage of this invention to provide a bubble trap which is structured by combining basic geometric shapes so that the resulting structure can be readily molded and easily assembled, so that it may be economically supplied for wide use, can be easily sterilized, and provides disposability.

Other purposes and advantages of this invention will become apparent from a study of the following portion of the specification, the claims and the attached drawings.

BRIEF DESCRIPTION OF THE DRAWINGS

FIG. 1 is a plan view of the first preferred embodiment of the bubble trap of this invention.

FIG. 2 is a bottom view thereof.

FIG. 3 is a central section through the bubble trap of FIG. 1 showing an optional filter therein.

FIG. 4 is an upward view under the cap of the bubble filter of FIG. 3, as seen generally along the line 4—4 of FIG. 3.

FIG. 5 is a view similar to FIG. 3 showing the bubble trap without the filter.

FIG. 6 is an enlarged similar view of the bubble trap, showing a space filler therein.

DESCRIPTION OF THE PREFERRED EMBODIMENTS

FIGS. 1, 2 and 3 show various views of the first preferred embodiment of the bubble trap of this invention for phase separating gas bubbles from flowing liquids. The bubble trap is generally indicated at 10 in these FIGURES. The bubble trap is made of two parts of injection-molded polymer composition material which are secured together. They are preferably made of clear, medical grade polycarbonate and are ultrasonically welded together to form the bubble trap 10. The two principal parts are body 12 and cover 14. Body 12 is principally a hollow housing 16 which is curved around the central axis 18 of the bubble trap 10. This central axis is normal to the sheet of drawing in FIGS. 1 and 2 and lies upright in the sheet in FIG. 3. Housing 16 is preferably substantially a circular cylindrical tube, but has some taper or draft to it in order to permit convenient molding. Towards the bottom of housing 16, step 20 is formed therein as a shape of revolution around the axis. Below step 20, floor 22 is substantially flat and sloped with respect to the axis. At the lowest point of the floor, barbed outlet tubular fitting 24 is provided. Outlet fitting 24 is off center from the axis and is downwardly directed parallel to the axis. The offset outlet eliminates the vortex which occurs with a center outlet. The vortex would suck in air bubbles to defeat the separation produced by the trap.

Center cone 26 is a hollow cone mounted on floor 22 and extending upwardly within the open interior of the housing. The purpose of the center cone is to reduce interior volume of the housing, and to provide a support for a filter. It also eliminates vortexing. Filter 32 is a conical accordion-pleated filter of woven synthetic polymer composition mesh or stainless steel wire mesh. The preferred mesh is a polyester monofilament woven screen having openings in the range of 20 to 60 microns and having a filament diameter in the 20 to 60 micron range. The filter fabric is described in more detail in George G. Siposs U.S. Pat. No. 4,344,777, the disclosure of which is incorporated herein by this reference. The filter must have sufficiently large mesh so as to pass blood cells with minimum trauma thereto, to hold back blood clots, and should hold back air or gas bubbles. Filter cover 34 closes the top of the filter, holds the filter in place, and engages upon the top of center cone 26 to firmly retain the filter in place.

The filter medium is preferably a polyester screen with uniform interstices of about 40 microns. The filter screen has about 25 percent open area. In order to support the polyester screen filter medium, polypropylene mesh of more coarse weave is used on each side of the filter mesh as support. This three-layer sandwich is pleated and configured in the truncated conical configuration and is potted between two end plates. The lower end plate 28 has an opening 30 therein which surrounds the center cone 26 and provides for downward outflow from the interior of the filter. Filter cover 34 is potted to the top of the filter fabric and may have a dimple therein to receive the top of the center cone to stabilize the filter. The bottom end plate 28 rests against the step 20 and is bonded thereto to secure the filter in place. The center cone thus also acts as a stabilizer for the filter to prevent accidental dislodgement during shipping and other vibrational stress.

The top of housing 16 terminates in flange 36, which has a side arm surface thereon extending away from the side of housing 16. Upwardly directed inlet fitting 38 is a barbed tubular inlet fitting similar to and lying parallel to outlet fitting 24. The inlet passageway 40 extends up through the inlet fitting and through the corresponding opening in the flange.

Cover 14 is also an injection-molded part of the same material. It has a flange 42 which overlies and is secured to flange 36, e.g. by ultrasonic welding as previously described. Cover 14 includes a cap 44 which overlies the housing 16. Cap 44 has an interior space which joins the interior space of the housing 16 to define the interior volume of the bubble trap. The interior space of cap 44 terminates in upwardly directed cone 46. Gas vent fitting 48 is at the top of the cap, on the center line, at the top of the cone. The gas vent fitting may be a Luer fitting and preferably is connected to a purge line with a check valve therein to prevent inflow of gas through the vent fitting into the body. Boss 50 is formed on the top of flange 42 and extends from inlet passage 40 to cap 44. It defines inlet passage 52 which joins the inlet passage 40 with the space under the cap. As is seen in FIGS. 1 and 4, the inlet passage 52 enters the cap in a direction so that it is tangential with the circular space defined under the cap.

The bubble trap 10 is preferably used in the arterial blood flow circuit, and the blood enters the trap through the vertically oriented inlet fitting 38 which has a conventional barbed configuration. The transition from the inlet passage 40 to the inlet passage 52 is with a smooth curve so that the inflowing blood turns into a horizontal direction and flows through the straight inlet passage 52 to the circular debubbling chamber 54 defined within cap 44 in housing 16. The tangential entry of the blood into the debubbling chamber 54 causes gentle rotation of the blood. This rotation causes the relatively lighter gas bubbles to congregate in the center of the chamber, with the upper portion of the chamber within the cover. The collected gas bubbles coalesce, rise and exit out of the gas vent fitting 48. The rotating blood gently descends into the lower part of the chamber which contains the filter. The blood flows through the filter and exits the housing through the vertically directed downward outlet fitting 24, which is also of barbed configuration so that conventional flexible tubing can be quickly installed on both the inlet and outlet fittings.

The circular debubbling chamber is above the filter element so that bubbles are separated from the blood and are removed through the vent before they come into contact with the filter element. In addition, wetted filters resist the passage of gas bubbles passing therethrough. This is because the surface tension of the blood covering the filter openings is quite strong and it would require a considerable trans-filter pressure differential to force the bubbles through the filter cloth. Thus, the filter serves as a backup protection against the transmittal of gas bubbles.

FIG. 5 shows bubble trap 60 as being formed of body 62 and cover 64. The body 62 and cover 64 are respectively identical to body 12 and cover 14 of the bubble trap 10. The difference is that bubble trap 60 does not have therein a filter to remove particles from the blood. Bubble trap 60 has the upwardly directed inlet fitting 66 which introduces inflowing liquid to tangential inlet passage 68 which tangentially introduces the liquid into the debubbling chamber 70. The general circular motion in the debubbling chamber causes the small gas bubbles to join and combine and rise to be exhausted out of vent fitting 72, which is at the top of the debubbling chamber under the conical cover where the gas bubbles concentrate. The down-flowing liquid passes down and out of outlet fitting 74, which is barbed like the inlet fittings 66 to be connectable to standard flexible tubing.

The center cone 76 reduces the volume of the debubbling chamber and inhibits vortexing by occupying the center and placement of the outlet fitting towards the circumferential edge of the debubbling chamber. Thus, the bubble trap 60 is identical to the bubble trap 10, except for the absence of the filter in bubble trap 60. Either of these bubble traps can be made smaller for pediatric service because of the lower flow rates in pediatric service.

Bubble trap 80, shown in FIG. 6, has an identical body and cover to those shown with respect to bubble traps 10 and 60 in FIGS. 1 and 5. Body 82 has the same interior debubbling chamber, interior cone 84 and off-center outlet fitting 86. Its cover 88 has the same uprightly directed inlet fitting 90 beside the debubbling chamber 92. Tangential inlet passage 94 tangentially directs the incoming liquid to the debubbling chamber. In the case of bubble trap 80, outlet check valve 96 is shown as mounted on vent fitting 98. When the vent fitting is of standard Luer configuration, Luer nut 100 is detachably attached thereto. Flexible tube 102 connects the nut with the outlet check valve 96 so that inflow of gas into the bubble trap is prevented. Such a structure can also be applied to the bubble traps 10 and 60. On the other hand, instead of venting to atmosphere, the flexible vent line 102 can be exhausted to a reservoir such as a cardiometry reservoir or oxygenator as long as it has a lower internal pressure than the bubble trap.

To reduce the interior volume of the bubble trap 80, the interior volume of the debubbling chamber can be reduced by the installation of filler 104. This is particularly useful in pediatric cases where the flow rate is lower and low priming volume is imperative. Filler 104 is comprised of upper and lower cases, interengaged together along their parting line and sealed together with appropriate means such as ultrasonic welding. The upper cup embraces the tip of cone 84, and the lower cup tightly embraces the base of the cone, above the floor 106 of body 82. The upper portion of the debubbling chamber remains at the same volume so that debubbling is properly achieved. Liquid velocity in the space between the filler and the outer wall of the body is no higher than that in an adult-sized unit operating at normal adult flow rates. Thus, no reduction in efficiency occurs, but blood volume is conserved.

The body of each bubble trap is sufficiently strong so that a clamp on the mast of cardio-pulmonary equipment can engage thereon so as to support the bubble trap in the upright position, permit the inlet and outlet arterial tubes to drape naturally, and keep rotation horizontal.

This invention has been described in its presently contemplated best modes, and it is clear that it is susceptible to numerous modifications, modes and embodiments within the ability of those skilled in the art and without the exercise of the inventive faculty. Accordingly, the scope of this invention is defined by the scope of the following claims:

What is claimed is:

1. A bubble trap for phase-separating gas bubbles from a flowing liquid comprising:

a body, said body being substantially a body of revolution about an upright axis, said body having a cover and a floor to define a debubbling chamber therein, an outlet in the upper portion of said debubbling chamber to permit the release of coalesced gas bubbles from said debubbling chamber;

an upwardly directed inlet fitting having an inlet passage therein, said inlet fitting being positioned beside said body, an inlet passage in said body connecting said inlet passage in said inlet fitting with said debubbling chamber, said inlet passage tangentially joining the walls defining said debubbling chamber so that fluid passing in through said inlet passage tangentially enters said debubbling chamber and rotates fluid around said axis in the counterclockwise direction in said debubbling chamber;

a central post mounted on said floor and extending upward on said axis to reduce volume in said debubbling chamber and eliminate vortexing on said axis; and an outlet connection on said body, said connection having an outlet passage therethrough adjoining said debubbling chamber between the wall of said body and said central post, said outlet passage being away from said axis to eliminate vortexing and being downwardly directed so that a naturally draping inlet hose can be connected to said inlet connection and a naturally draping outlet hose can be connected to said outlet connection.

2. The bubble trap of claim 1 wherein said floor of said debubbling chamber is at an angle with respect to said axis and is substantially planar, said floor being lowest at said outlet connection.

3. The bubble trap of claim 1 further including a filter within said debubbling chamber, said filter being positioned around said post and being mounted so that fluid passing from said debubbling chamber through said filter passes towards said outlet connection.

4. The bubble trap of claim 3, whrein said filter is an accordion-pleated filter of circular conical configuration and an open interior, a filter cover secured to the top of said filter to prevent flow into the interior of said filter without passing through said filter, said filter having a bottom end plate thereon, said bottom end plate being closed with respect to said debubbling chamber, said bottom plate having an opening therein in communication with said outlet fitting so that all liquid flow through said filter passes through said filter.

5. The bubble trap of claim 4 wherein said filter is a woven mono-filament filter cloth having openings of substantially 40 microns in size.

6. The bubble trap of claim 5 wherein a support mesh having openings larger than 40 microns is positioned on each side of said filter cloth to support said filter cloth in said filter.

7. The bubble trap of claim 1 wherein a space filler of shape which is circular around said axis is mounted on said post to fill a portion of the space within said debubbling chamber.

8. A bubble trap for phase-separating gas bubbles from flowing liquid comprising:

a body having interior walls defining a chamber therein, said interior walls being circular about an upright axis, a flange on the top of said body, a floor defining the bottom of said chamber, said floor lying at an acute angle with respect to said axis, an outlet fitting on said body, said outlet fitting being mounted on said floor at the lowest portion thereof, a post mounted on said floor and extending upwardly from said floor, said post being centrally axially mounted within said debubbling chamber so that said outlet fitting is between said post and said body wall, said outlet fitting being substantially parallel to said axis and being beside said axis and beside said central post, said outlet fitting having walls therein defining an outlet passage and defining the downward direction of said bubble trap, said outlet fitting being downwardly directed;

a cover on said body, a flange on said cover, said flange on said cover being attached to said flange on said body to attach said cover to said body, said cover having walls enclosing the top of said chamber, said walls and said cover being substantially circular about said axis and in line with said chamber walls in said body to define a debubbling chamber within said body;

an inlet structure formed as part of said cover including walls in said flange on said cover and said flange on said body defining said inlet passage into said debubbling chamber so that when said flanges are secured together said inlet fitting can deliver liquid through said inlet passage tangentially into said debubbling chamber, said inlet structure having an inlet fitting secured to said flange on said body substantially parallel to said axis and beside said axis and directed downwardly with respect to said chamber, an inlet passage extending through said inlet fitting to said debubbling chamber, said inlet passage joining said debubbling chamber substantially tangentially to the circular walls defining said debubbling chamber so that inflowing liquid containing entrained bubbles will rotate counterclockwise in said debubbling chamber substantially about said axis to bring at least some of the bubbles together adjacent said axis so that the bubbles can rise in said debubbling chamber, an outlet vent fitting at the top of said debubbling chamber to vent bubbles coalesced in the center of fluid rotating in said debubbling chamber and to pass debubbled liquid downward through debubbling chamber out of said outlet; and a filter mounted within said body, said filter being an accordion-folded circular filter having a filter cover and a bottom plate, said filter cover engaging on said post and said filter bottom plate engaging against said walls defining said debubbling chamber within said body.

9. The bubble trap of claim 8 wherein a hollow filler structure is mounted on said post to occupy some of the volume of said debubbling chamber.

10. The bubble trap of claim 8 wherein a filter cover is engaged on the top of said filter and a filter bottom plate is engaged under said filter and there is, a step in said walls defining said chamber in said body, said filter bottom plate engaging on said step, said filter cover being closed and said filter bottom plate being open within said filter so that downwardly flowing liquid must pass through said filter to read said outlet.

* * * * *